United States Patent [19]

Rodewald

[11] 4,066,714

[45] Jan. 3, 1978

[54] MANUFACTURE OF LIGHT OLEFINS

[75] Inventor: Paul G. Rodewald, Rocky Hill, N.J.

[73] Assignee: Mobil Oil Corporation, New York, N.Y.

[21] Appl. No.: 638,403

[22] Filed: Dec. 8, 1975

[51] Int. Cl.² .......................... C07C 1/20; C07C 11/02
[52] U.S. Cl. .................................................... 260/682
[58] Field of Search ........................... 260/682, 668 R

[56] References Cited

U.S. PATENT DOCUMENTS

| | | | |
|---|---|---|---|
| 3,529,033 | 9/1970 | Frilette et al. | 260/682 |
| 3,894,106 | 7/1975 | Chang et al. | 260/682 |
| 3,894,107 | 7/1975 | Butter et al. | 260/673 |

Primary Examiner—C. Davis
Attorney, Agent, or Firm—Charles A. Huggett; Raymond W. Barclay

[57] ABSTRACT

A catalytic process is provided for converting lower monohydric alcohols and their ethers, especially methanol and dimethyl ether, to a hydrocarbon mixture rich in $C_2$-$C_3$ olefins, by contact, under conversion conditions, with a catalyst comprising a crystalline aluminosilicate zeolite having a silica to alumina mole ratio of at least about 12, a constraint index, as hereinafter defined, within the approximate range of 1 to 12 and containing, in cationic form, between about 0.01 and about 1.9 milliequivalents per gram of one or more metals characterized by an ionic radius exceeding 1 Angstrom.

7 Claims, 1 Drawing Figure

- ● CsZSM-5 (1-2μ, .315 meq, Cs/gram)
- ▲ HZSM-5 (1-2μ)
- ■ NaZSM-5 (1-2μ, .315 meq, Na/gram)

MANUFACTURE OF LIGHT OLEFINS

BACKGROUND OF THE INVENTION

1. Field of the Invention

This invention relates to a process for the conversion of low molecular weight monohydric alcohols or ethers to light olefins in the presence of a crystalline aluminosilicate zeolite-containing catalyst.

2. Description of the Prior Art

A remarkable growth in the production of synthetic fibers, plastics and rubber has taken place in recent decades. This growth, to a very large extent, has been supported and encouraged by an expanding supply of inexpensive petrochemical raw materials such as ethylene, propylene, benzene, toluene and xylenes. Accompanying this remarkable development there has been an increasing demand for aromatic hydrocarbons for use as high octane gasoline components. Environmental factors which limit the lead content of gasoline are likely to aggravate the need for aromatics.

Increasing demand for olefins, e.g. $C_2$-$C_3$ olefins and for aromatic hydrocarbons, e.g. para-xylene, has, from time to time, led to periods of shortage, either due to a diminished supply of suitable feedstocks or to limited processing capacity. In any event, it would appear desirable to provide efficient means for converting raw materials other than petroleum to olefins and aromatic hydrocarbons.

SUMMARY OF THE INVENTION

In accordance with the present invention, there has been discovered a process which produces valuable light olefinic hydrocarbons and also mononuclear aromatics with high selectivity for para-xylene formation. The present process involves conversion of lower monohydric alcohols having up to four carbon atoms, their ether derivatives or mixtures of any of these by contact at elevated temperatures with a catalyst comprising a crystalline aluminosilicate zeolite, which zeolite has a silica to alumina ratio of at least about 12, a constraint index within the approximate range of 1 to 12 and contains, in cationic form, between about 0.01 and about 1.9 milliequivalents per gram of one or more metals characterized by an ionic radius exceeding 1 Angstrom.

It has been found that use of such zeolite catalysts afford a substantially higher selectivity for ethylene production over corresponding use of the sodium form of the zeolite. It has further been found that with the catalysts described herein only moderate amounts of durene are formed during the desired alcohol and/or ether conversion. As is well known, durene is an undesirable component in gasoline, tending to crystallize in the carburetor of an internal combustion engine causing the latter to stall. High durene make, usually associated with low operating temperatures during conversion of low molecular weight alcohols has not been observed using the catalysts described herein.

The alcohols may be manufactured from synthesis gas, i.e. a mixture of CO and $H_2$, from coal or they may be produced by fermentation or they may be manufactured from petroleum fractions in excess supply.

The present process comprises conversion of such alcohols and/or ethers in the presence of the specific catalyst at a temperature between about 250° and about 600° C. and preferably between about 300° and about 500° C. at a pressure between about 0.2 and about 30 atmospheres utilizing a feed liquid hourly space velocity (LHSV) between about 0.1 and about 20. The latter LHSV is based upon the volume of catalyst composition, i.e. total volume of active catalyst and binder therefor. The effluent is separated and distilled to remove the desired products of light olefinic hydrocarbons and aromatics, such as para-xylene. Any unreacted product may be recycled for further reaction.

BRIEF DESCRIPTION OF THE DRAWING

The single FIGURE of the drawing is a plot of ethylene selectivity against hydrocarbon yield for methanol conversion under comparable conditions using various zeolite catalysts.

DESCRIPTION OF SPECIFIC EMBODIMENTS

Figure 1:
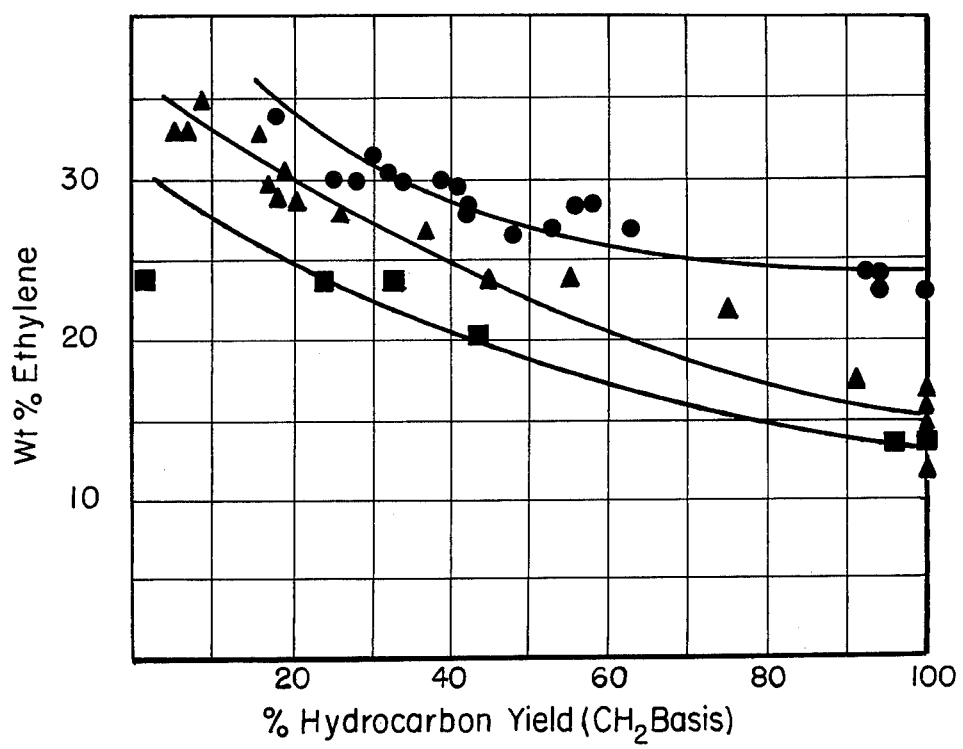

It is contemplated that any monohydric alcohol having from 1 to 4 carbon atoms or ethers derived from these alcohols may be used as feed to the process of this invention. Thus, methanol, ethanol, n-propanol, isopropanol, n-butanol, sec-butanol and isobutanol may be used either alone or in admixture with ethers derived from such alcohols. Likewise, the noted ethers, e.g. methyl-ethyl ether may be similarly used. Particularly preferred feeds are methanol, dimethyl ether and mixtures thereof.

In accordance with the present invention, such feed is brought into contact, under conversion conditions, with a bed comprising particle-form catalyst containing a crystalline aluminosilicate zeolite having: (1) a silica to alumina ratio of at least about 12, (2) a constraint index within the approximate range of 1 to 12 and (3) cationic metal of greater than 1 Angstrom in ionic radius present in an amount of between about 0.01 and about 1.9 milliequivalents per gram of zeolite. The particular milliequivalent of specific cationic metal within the aforenoted range will depend on the silica to alumina ratio of the parent zeolite. With the use of lower milliequivalents of metals higher silica to alumina zeolites will be employed and conversely with the use of higher milliequivalents of metal lower silica to alumina zeolites will be employed; it being understood that in every instance a zeolite having a silica to alumina ratio of at least about 12 is employed.

The zeolites herein described are members of a novel class exhibiting some unusual properties. These zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather then attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U. S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974, and now abandoned. This zeolite can be identified, in terms of mole ratios of oxides and in the anhydrous state, as follows:

$(0.3-2.5)R_2O : (0-0.8)M_2O : Al_2O_3 : > 8 SiO_2$ wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4\text{--}2.5)R_2O : (0\text{--}0.6) M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d (A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing source of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH−/SiO₂ | 0.05–0.5 | 0.07–0.49 |
| H₂O/OH− | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3\text{--}2.5)R_2O : (0\text{--}0.8)M_2O : Al_2O_3 : > 8 SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

$$(0.4\text{--}2.5)R_2O : (0.0.6) M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d (A) | I/Io |
|---|---|
| 9.6 ± 0.20 | Very Strong–Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |

TABLE II-continued

| d (A) | I/Io |
|---|---|
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH−/SiO₂ | 0.05–0.5 | 0.07–0.49 |
| H₂O/OH− | 41–500 | 100–250 |
| SiO₂/Al₂O₃ | 8.8–200 | 12–60 | wherein R is an organic nitrogen-containing cation derived from pyrrolidone or ethylenediamine and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possible because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The crystal size of the synthesized zeolite has been found to be an important factor influencing the desired conversion of low monohydric alcohol and/or ether to light olefinic hydrocarbons. In general while the crystal size can be within the approximate range of 0.02 to 2 microns, it is preferred that large crystals, i.e. between about 1 and about 2 microns in size be employed. With the use of crystals within such size range, i.e. 1–2 microns, higher selectivity for production of $C_2$-$C_3$ olefins and particularly ethylene has been observed.

When synthesized in the sodium form, the zeolite is conveniently converted to the desired metal form, i.e. to a zeolite of one or more cationic metals of ion radius greater than 1 Angstrom, by ion exchange. The resulting zeolite should be substantially free of sodium, i.e. contain less than about 1.5 weight percent sodium. Ion exchange may take place by contacting the synthesized sodium form of the zeolite with a solution of an ionizable compound of a metal having an ionic radius exceeding 1 Angstrom. Representative of such metals are potassium, rubidium, cesium, strontium, barium, lanthanum, gold, silver, mercury, gallium, tin, lead, indium and thallium.

The ionic radii of these metals are shown below:

|  | Ionic Radius In Angstroms |
|---|---|
| Potassium | 1.33 |
| Rubidium | 1.48 |
| Cesium | 1.69 |
| Strontium | 1.13 |
| Barium | 1.35 |
| Lanthanum | 1.15 |
| Gold | 1.37 |
| Silver | 1.26 |
| Mercury | 1.10 |
| Gallium | 1.48 |
| Tin | 1.12 |
| Lead | 1.20 |
| Indium | 1.32 |
| Thallium | 1.40 |

Of this group, the monovalent metals are preferred and particularly potassium, rubidium, cesium, silver and gold. The amount of such metal introduced into the zeolite, in cationic form, is generally between about 0.01 and about 1.9 milliequivalents per gram and preferably between about 0.05 and about 0.5 milliequivalents per gram. As an alternative method of ion exchange, the initially formed sodium zeolite may be converted to the hydrogen form generally by intermediate formation of the ammonium form as a result of ammonium ion exchange and calcination of the ammonium form to yield the hydrogen form or the ammonium form may be exchanged directly. The resulting hydrogen or ammonium form may thereafter be ion exchanged with a compound, generally an aqueous solution, containing one or more of the above noted metal ions having an ionic radius of greater than 1 Angstrom.

In practicing the desired conversion process, it may be desirable to incorporate the above-described metal exchanged zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided metal exchanged zeolite and inorganic oxide gel matrix may vary widely with the zeolite content ranging from between about 1 to about 99 percent by weight and more usually in the range of about 5 to about 80 percent by weight of the composite.

The process of this invention is conducted such that alcohol and/or ether conversion is carried out in the vapor phase by contact in a reaction zone, such as for example, a fixed bed of catalyst, under effective conversion conditions, said catalyst being characterized as above defined.

The alcohol and/or ether conversion process described herein may be carried out as a batch-type, semi-continuous or continuous operation utilizing a fixed or moving bed catalyst system. A preferred embodiment entails use of a catalyst zone wherein the alcohol or ether charge is passed concurrently or countercurrently through a moving bed of particle-form catalyst. The latter after use is conducted to a regeneration zone wherein coke is burned from the catalyst in an oxygen-containing atmosphere, e.g. air, at an elevated temperature, after which the regenerated catalyst is recycled to the conversion zone for further contact with the alcohol and/or ether feed.

The product stream in the process of this invention contains steam and a hydrocarbon mixture particularly rich in light olefins, ethylene and propylene and aromatic hydrocarbons. Generally, a major fraction of the total olefins calculated on a mole basis, is ethylene plus propylene; and a major fraction of these two olefins is ethylene. The predominant aromatic hydrocarbons are monocyclic hydrocarbons such as benzene, toluene and xylenes. Thus, the predominant hydrocarbons are all valuable petrochemicals. The steam and hydrocarbons are separated from one another by methods well known in the art.

The following examples will serve to illustrate the process of the invention without limiting the same:

EXAMPLE 1

42.2 pounds of Q-Brand sodium silicate were mixed with 52.8 pounds of water. The resulting solution was designated Solution A. 1.35 pounds of commercial grade aluminum sulfate ($Al_2(SO_4)_3$.14 $H_2O$), 15.84 pounds of commercial grade NaCl, and 3.52 pounds of $H_2SO_4$ (96.06wt % $H_2SO_4$) were mixed with 72.2 pounds of water. The resulting solution was designated Solution B. Solution A and Solution B were mixed simultaneously in a nozzle and sprayed into an autoclave equipped with a paddle agitator. 2.84 pounds of tri-n-propyl bromide were added to the contents of the autoclave. The mixture was reacted at 316° F. with 121 rpm agitation. After 14.1 hours at 316° F., the solid product was analyzed by X-ray diffraction and found to be 100% ZSM-5.

A 1 gram sample of the ammonium form of the above prepared ZSM-5 containing 0.45 meq. of ammonium ion was stirred for one hour with 3.15 cc of 0.1000 M CsOH solution (.315 meq. Cs). Ammonia was evolved and was removed by a slow nitrogen stream. The product was filtered and calcined at 1° C/min. to 538° C. then six hours at 538° C. The catalyst was pelleted and sized to 14–30 mesh.

EXAMPLE 2

2.4 parts by weight of methanol were contacted with 1.0 part by weight of the CsZSM-5 catalyst prepared as in Example 1 at a temperature of 320° C. and a liquid hourly space velocity of 1.8 for a 34 percent conversion of the methanol feed. Gas chromatographic analysis of the product mixture is shown hereafter in Table III.

EXAMPLE 3

2.4 parts by weight of methanol were contacted with 1.0 part by weight of the CsZSM-5 catalyst prepared as in Example 1 at a temperature of 345° C. and a liquid hourly space velocity of 1.8 for a 100 percent conversion of the methanol feed. Gas chromatographic analysis of the product mixture is shown below in Table III.

TABLE III

| Component | Example 2 | Example 3 |
| --- | --- | --- |
| Methane | 0.3 | 0.3 |
| Ethane | 0.1 | 0.1 |
| Ethylene | 30 | 23 |
| Propane | 2.0 | 2.7 |
| Propylene | 24 | 9.5 |
| Iso-Butane | 5.7 | 6.6 |
| N-Butane | 0.7 | 0.8 |
| Butenes | 13 | 13 |
| Penetenes (a) | 6.7 | 8.8 |
| Hexenes (a) | 4.4 | 6.0 |
| Benzene (b) | — | 4.0 |
| Toluene | — | 7.6 |
| Ethylbenzene | 0.3 | 0.3 |
| Xylenes (c) | 6.0 | 5.2 |
| $C_9^+$ (d) | 6.0 | 12 |

(a) Including ~ 1-2% paraffin
(b) At low conversion benzene and toluene peaks are not resolved from dimethylether and methanol peaks
(c) p-xylene content varied from 50-80%
(d) Durene varied from 1-3%.

It will be seen from the above results that use of a catalyst of the type described hereinabove afforded high selectivity for the production of $C_2$-$C_3$ olefins and particularly ethylene.

EXAMPLE 4

A NaZSM-5 catalyst of 1-2 μ crystal size was prepared as in Example 1 using 0.1000N NaOH solution in place of 0.1000N CsOH solution. Methanol (2.4 parts by weight) was contacted with NaZSM-5 (1.0 part by weight) at a liquid hourly space velocity of 1.5. The conversion was 33% at 410° C and 100% at 430° C. Gas chromatographic analysis of the product at 100% conversion is shown below in Table IV.

EXAMPLE 5

Methanol (2.4 parts by weight) was contacted with 1-2 μ HZSM-5, prepared by calcination of the ammonium form described in Example 1, (1.0 part by weight) at a liquid hourly space velocity of 1.3. The conversion was 38% at 320° C and 98% at 350° C. Gas chromatographic analysis of the product at 98% conversion is shown below in Table IV.

TABLE IV

| | Example 4 | Example 5 |
| --- | --- | --- |
| Methane | 0.9 | 0.5 |
| Ethane | 0.1 | 0.2 |
| Ethylene | 14 | 14 |
| Propane | 2.0 | 4.8 |
| Propylene | 18 | 5.2 |
| Iso-Butane | 8.9 | 9.2 |
| N-Butane | 0.7 | 1.9 |
| Butenes | 18 | 17 |
| Pentenes (a) | 13 | 13 |
| Hexenes (a) | 6.4 | 7.2 |
| Benzene | 3.1 | 2.8 |
| Toluene | 4.2 | 2.8 |
| Ethylbenzene | 0.3 | 0.5 |
| Xylenes | 7.6 | 9.4 |
| $C_9^+$ | 3.2 | 11.1 |

(a) Including ~1-2% paraffin

The comparative results of ethylene selectivity vs. hydrocarbon yield ($CH_2$ base) for the catalysts Cs ZSM-5, HZSM-5 and Na ZSM-5 (each 1-2 microns crystal size) is shown graphically in FIG. 1. "$CH_2$ basis" has reference to the $CH_2$ content of the organic product. Referring more particularly to this figure, it will be evident that with the use of the CsZSM-5 catalyst, ethylene production was high, with ethylene selectivity being maintained at high conversion. The HZSM-5 curve with approximately 10 percent lower selectivity at low conversion which decreases to 40 percent lower selectivity at high conversion. The Na ZSM-5 curve is well below the CsZSM-5 curve with approximately 30 to 45 percent lower selectivity in all instances.

EXAMPLE 6

Methanol (2.4 parts by weight) were contacted with 1 part by weight of CsZSM-5 catalyst containing 0.315 meq. cesium per gram prepared in a manner similar to that of Example 1 but characterized by a crystal size of 0.02–0.05 micron in one instance and a crystal size of 0.2–0.5 micron in a second instance. The conditions included temperatures of 280°–370° C and a liquid hourly space velocity of 1.8. The ethylene selectivity, i.e. the weight percent ethylene in the resulting hydrocarbon product at 100 percent conversion, obtained, together with comparable results obtained using the hydrogen form of the zeolite are set forth in Table V below:

TABLE V

| Catalyst | Crystal Size | Temp. ° C. | Ethylene Selectivity |
| --- | --- | --- | --- |
| HZSM-5 | 0.02–0.05 | 280 | 8% |
| CsZSM-5 | 0.02–0.05 | 330 | 14% |
| HZSM-5 | 0.2 –0.5 | 310 | 8% |
| CsZSM-5 | 0.2 –0.5 | 370 | 13% |

The above results show a definite improvement in ethylene selectivity attained by incorporating cesium in HZSM-5.

EXAMPLE 7

A BaZSM-5 catalyst of 1-2 μ crystal size was prepared as in Example 1 using 0.1000N barium hydroxide in place of cesium hydroxide and contained 0.22 meq. barium/gram.

Methanol (2.4 parts by weight) was contacted with 1 part by weight of the BaZSM-5 catalyst at a temperature of 340° C and a liquid hourly space velocity 1.2 for a 100 percent conversion of the methanol feed. Under comparable conditions, a 20 percent increase in ethylene selectivity, i.e. from 14 percent to 17 percent, was observed for the barium form of ZSM-5 over the corresponding hydrogen form.

It is to be understood that the foregoing description is merely illustrative of preferred embodiments of the invention of which many variations may be made by those skilled in the art within the scope of the following claims without departing from the spirit thereof.

I claim:

1. A process for producing hydrocarbons which comprises contacting, under conversion conditions, a charge consisting essentially of one or more lower monohydric alcohols having up to four carbon atoms, the ethers derived therefrom, or mixtures of said alcohols and ethers with a catalyst comprising a crystalline aluminosilicate zeolite having a crystal size within the approximate range of 1 to 2 microns, a silica to alumina ratio of at least about 12, a constraint index within the approximate range of 1 to 12 and containing, in cationic form, between about 0.01 and about 1.9 milliequivalents per gram of a metal selected from the group consisting of cesium and barium.

2. The process of claim 1 wherein said conversion conditions include a temperature of 250° to 600° C., a pressure from about 0.2 to about 30 atmospheres and a liquid hourly space velocity of between about 0.1 and about 20.

3. The process of claim 2 wherein said charge is methanol, dimethyl ether or mixtures thereof.

4. The process of claim 1 wherein said crystalline aluminosilicate zeolite is ZSM-5.

5. The process of claim 1 wherein said metal is cesium.

6. The process of claim 1 wherein said crystalline aluminosilicate zeolite is CsZSM-5.

7. The process of claim 1 wherein said crystalline aluminosilicate zeolite is BaZSM-5.

* * * * *